United States Patent
Bonnet et al.

(10) Patent No.: US 9,981,891 B2
(45) Date of Patent: May 29, 2018

(54) PROCESS FOR PRODUCING 1-CHLORO-2,2-DIFLUOROETHANE

(71) Applicant: ARKEMA FRANCE, Colombes (FR)

(72) Inventors: Philippe Bonnet, Lyons (FR); Bertrand Collier, Saint-genis-laval (FR); Dominique Garrait, Charly (FR); Pierre-Marie Sedat, Fleurieux sur L'arbresle (FR)

(73) Assignee: ARKEMA FRANCE, Colombes (FR)

( * ) Notice: Subject to any disclaimer, the term of this patent is extended or adjusted under 35 U.S.C. 154(b) by 0 days. days.

(21) Appl. No.: 15/101,733

(22) PCT Filed: Nov. 28, 2014

(86) PCT No.: PCT/FR2014/053083
§ 371 (c)(1),
(2) Date: Jun. 3, 2016

(87) PCT Pub. No.: WO2015/082812
PCT Pub. Date: Jun. 11, 2015

(65) Prior Publication Data
US 2017/0267612 A1   Sep. 21, 2017

(30) Foreign Application Priority Data

Dec. 4, 2013 (FR) .................................. 13 62095

(51) Int. Cl.
*C07C 17/20* (2006.01)

(52) U.S. Cl.
CPC ................... *C07C 17/206* (2013.01)

(58) Field of Classification Search
CPC ....... C07C 19/12; C07C 17/21; C07C 17/206; C07C 17/35; B01J 23/862; B01J 27/138; B01J 37/26; B01J 23/06
See application file for complete search history.

(56) References Cited

U.S. PATENT DOCUMENTS

| | | | |
|---|---|---|---|
| 2002/0183569 A1 | 12/2002 | Bolmer et al. | |
| 2005/0228202 A1* | 10/2005 | Nappa ................... | B01J 23/864 570/161 |
| 2014/0330051 A1* | 11/2014 | Lui ......................... | B01J 23/862 570/161 |

FOREIGN PATENT DOCUMENTS

| | | | |
|---|---|---|---|
| EP | 1 008 575 A1 | | 6/2000 |
| FR | 2 783 820 A1 | | 3/2000 |
| FR | 2 783 821 A1 | | 3/2000 |
| WO | WO 99/07470 | * | 2/1999 |
| WO | WO 2013/053800 A2 | | 4/2013 |

OTHER PUBLICATIONS

International Search Report (PCT/ISA/210) dated Mar. 5, 2015, by the European Patent Office as the International Searching Authority for International Application No. PCT/FR2014/053083.
Written Opinion (PCT/ISA/237) dated Mar. 5, 2015, by the European Patent Office as the International Searching Authority for International Application No. PCT/FR2014/053083.

* cited by examiner

*Primary Examiner* — Jafar Parsa
(74) *Attorney, Agent, or Firm* — Buchanan Ingersoll & Rooney P.C.

(57) ABSTRACT

The present invention relates to the field of saturated fluorohydrocarbons. The subject matter thereof is more particularly the production of 1-chloro-2,2-difluoroethane from 1,1,2-trichloroethane and/or 1,2-dichloroethylene. A process for producing 1-chloro-2,2-difluoroethane from 1,1,2-trichloroethane and/or 1,2-dichloroethylene including (i) at least one step during which the 1,1,2-trichloroethane and/or the 1,2-dichloroethylene reacts or react with hydrofluoric acid in the gas phase, optionally in the presence of an oxidizing agent, in the presence or in the absence of a fluorination catalyst, to give a stream including 1-chloro-2,2-difluoroethane, hydrochloric acid, hydrofluoric acid and at least one C compound(s) chosen from 1-chloro-2-fluoroethylenes (cis and trans), 1,2-dichloro-2-fluoroethane and, optionally, unreacted 1,1,2-trichloroethane and/or 1,2-dichloroethylene.

16 Claims, No Drawings

PROCESS FOR PRODUCING 1-CHLORO-2,2-DIFLUOROETHANE

The present invention relates to the field of saturated fluorohydrocarbons. The invention relates more particularly to the manufacture of 1-chloro-2,2-difluoroethane from 1,1,2-trichloroethane.

1-Chloro-2,2-difluoroethane (HCFC-142) is not only known as an expander in the manufacture of foams, but also as a starting material in the manufacture of pharmaceutical or agrochemical compounds.

It is known practice to prepare 1-chloro-2,2-difluoroethane by reacting 1,1,2-trichloroethane (HCC-140) with hydrofluoric acid in the liquid phase, at a temperature of between 30 and 180° C. and in the presence of a Lewis acid as catalyst (FR 2 783 821). The preparation of HCFC-142 may also be performed in the gas phase at a temperature of between 120 and 400° C., in the presence of a bulk or supported chromium-based catalyst (FR 2 783 820 and EP 1 008 575).

Moreover, WO 2013/053800 describes the preparation of catalysts for the fluorination of HCC-140 and 1,2-dichloroethylene (1130) with hydrofluoric acid, said catalysts being obtained by co-depositing ferric chloride and magnesium chloride on chromium oxide and alumina oxide or by co-depositing chromium nitrate and nickel nitrate on active charcoal or by doping alumina with zinc chloride.

It is observed from WO 2013/053800 that all the tests were performed over a very short time (maximum of 6 hours) and that the fluorination of HCC-140 in the majority of the cases leads predominantly to 1,2-dichloroethylene (isomers not specified).

The Applicant has developed a process for manufacturing 1-chloro-2,2-difluoroethane which does not have the drawbacks of the prior art.

The present invention provides a process for manufacturing 1-chloro-2,2-difluoroethane from 1,1,2-trichloroethane and/or 1,2-dichloroethylene, comprising (i) at least one step during which 1,1,2-trichloroethane and/or 1,2-dichloroethylene react(s) with hydrofluoric acid in the gas phase and in the presence or absence of a fluorination catalyst, to give a stream comprising 1-chloro-2,2-difluoroethane, hydrochloric acid, hydrofluoric acid and at least one compound C chosen from 1-chloro-2-fluoroethylenes (cis and trans), 1,2-dichloro-2-fluoroethane and optionally unreacted 1,1,2-trichloroethane and/or 1,2-dichloroethylene.

One subject of the present invention is thus a process for manufacturing 1-chloro-2,2-difluoroethane from 1,1,2-trichloroethane, comprising (i) at least one step during which 1,1,2-trichloroethane reacts with hydrofluoric acid in the gas phase in the presence or absence of a fluorination catalyst, to give a stream comprising 1-chloro-2,2-difluoroethane, hydrochloric acid, hydrofluoric acid and at least one compound C chosen from 1,2-dichloroethylenes (cis and trans), 1-chloro-2-fluoroethylenes (cis and trans), 1,2-dichloro-2-fluoroethane and optionally unreacted 1,1,2-trichloroethane, (ii) at least one step of separating the compounds derived from the reaction step to give a stream A comprising hydrochloric acid and a stream B comprising hydrofluoric acid, 1-chloro-2,2-difluoroethane, at least one compound C and optionally 1,1,2-trifluoroethane, (iii) at least one step of separating the stream B to give an organic phase comprising 1-chloro-2,2-difluoroethane, at least one compound C and optionally unreacted 1,1,2-trichloroethane and a non-organic phase predominantly comprising HF, (iv) at least one step of separating the 1-chloro-2,2-difluoroethane from the organic phase obtained in (iii), (v) optional recycling into step (i) of the organic phase after the separation of step (iv), and (vi) optional recycling into step (i) of the non-organic phase derived from step (iii).

A catalyst is preferably used in step (i) and advantageously in the presence of an oxidizing agent.

After separating out the 1-chloro-2,2-difluoroethane, the organic phase preferably comprises 1-chloro-2-fluoroethylene, 1,2-dichloroethylenes (cis and trans) and 1,2-dichloro-2-fluoroethane.

According to one embodiment, before recycling into step (i), the non-organic phase obtained in (iii) is purified such that the HF content is greater than or equal to 90% by weight. Preferably, this purification comprises at least one distillation, advantageously performed at a temperature of between −23 and 46° C. and an absolute pressure of between 0.3 and 3 bar.

Preferably, the separation step (ii) comprises at least one distillation, advantageously performed at a temperature of between −60° and 120° C. and more particularly between −60 and 89° C. and an absolute pressure of between 3 and 20 bar and advantageously between 3 and 11 bar.

Preferably, the separation step (iii) comprises at least one decantation step, advantageously performed at a temperature of between −20 and 60° C. and more particularly between −20 and 10° C.

Preferably, the separation step (iv) comprises at least one distillation, advantageously performed at a temperature of between 10 and 115° C. and more particularly between 35 and 79° C. and an absolute pressure of between 0.3 and 4 bar, advantageously between 1 and 4 bar.

This separation step may be performed by extractive azeotropic distillation, liquid/liquid extraction or membrane separation.

The temperature of the reaction step is preferably between 150 and 400° C., advantageously between 200 and 350° C.

The pressure at which the fluorination reaction is performed is preferably between 1 and 30 bar absolute, advantageously between 3 and 20 bar absolute and more particularly between 3 and 15 bar.

The amount of hydrofluoric acid used in the reaction is preferably between 5 and 40 mol and advantageously between 10 and 30 mol per mole of HCC-140 and/or 1,2-dichloroethylene.

The contact time, defined as being the volume of catalyst/total gas flow rate by volume at the reaction temperature and pressure, may be between 2 and 200 seconds, preferably between 2 and 100 seconds, advantageously between 2 and 50 seconds.

The oxidizing agent, in pure form or mixed with nitrogen, may be chosen from oxygen and chlorine. Chlorine is preferably chosen.

The amount of oxidizing agent used is preferably between 0.01 mol % and 20 mol % per mole of F140 or F1130, advantageously between 0.01 mol % and 0.2 mol % per mole of HCC-140 and/or 1,2-dichloroethylene.

An amount of oxidizing agent of between 1-10 mol % relative to F140 or F1130 gave very promising results.

The catalyst used may be in bulk or supported form. The catalyst may be based on a metal, especially a transition metal or an oxide, halide or oxyhalide derivative of such a metal. Examples that may be mentioned are especially $FeCl_3$, chromium oxyfluoride, $NiCl_2$ and $CrF_3$, and mixtures thereof.

Supported catalysts that may be mentioned include those supported on charcoal or based on magnesium, such as magnesium derivatives, especially halides such as $MgF_2$ or magnesium oxyhalides such as oxyfluorides or based on aluminum such as alumina, activated alumina or aluminum derivatives, especially halides, such as $AlF_3$ or aluminum oxyhalides such as oxyfluoride.

The catalyst may also comprise co-catalysts chosen from Co, Zn, Mn, Mg, V, Mo, Te, Nb, Sb, Ta, P, Ni, Zr, Ti, Sn, Cu, Pd, Cd, Bi and rare-earth metals or mixtures thereof. When the catalyst is based on chromium, Ni, Mg and Zn are advantageously chosen as co-catalyst.

The co-catalyst/catalyst atomic ratio is preferably between 0.01 and 5.

Chromium-based catalysts are particularly preferred.

The catalyst used in the present invention may be prepared by coprecipitation of the corresponding salts optionally in the presence of a support.

The catalyst may also be prepared by comilling of the corresponding oxides.

Prior to the fluorination reaction, the catalyst is subjected to a step of activation with HF at a temperature preferably between 100 and 450° C., advantageously between 200 and 400° C. for a time of between 1 and 50 hours.

Besides the treatment with HF, the activation may be performed in the presence of the oxidizing agent.

The activation steps may be performed at atmospheric pressure or at a pressure of up to 20 bar.

According to a preferred mode of the invention, the support may be prepared using high-porosity alumina. In a first step, the alumina is converted into aluminum fluoride or a mixture of aluminum fluoride and alumina, by fluorination using air and hydrofluoric acid, the degree of conversion of the alumina into aluminum fluoride depending essentially on the temperature at which the fluorination of the alumina is performed (in general between 200° C. and 450° C., preferably between 250° C. and 400° C.). The support is then impregnated using aqueous solutions of salts of chromium, nickel and optionally a rare-earth metal, or using aqueous solutions of chromic acid, of nickel or zinc salts, and optionally of rare-earth metal salts or oxides and methanol (serving as chromium-reducing agent). As chromium, nickel or zinc and rare-earth metal salts, use may be made of chlorides or other salts, for instance nickel and rare-earth metal oxalates, formates, acetates, nitrates and sulfates or dichromate, provided that these salts are soluble in the amount of water that can be absorbed by the support.

The catalyst may also be prepared by direct impregnation of alumina (which is generally activated) using solutions of the chromium, nickel or zinc compounds, and optionally the rare-earth metal compounds, mentioned above. In this case, the conversion of at least part (for example 70% or more) of the alumina into aluminum fluoride or aluminum oxyfluoride takes place during the step of activation of the metal of the catalyst.

The activated aluminas that may be used for the preparation of the catalyst are well-known, commercially available products. They are generally prepared by calcination of alumina hydrates (aluminum hydroxides) at a temperature of between 300° C. and 800° C. The aluminas (activated or non-activated) may contain large amounts (up to 1000 ppm) of sodium without this harming the catalytic performance.

Preferably, the catalyst is conditioned or activated, i.e. converted into constituents that are active and stable (with respect to the reaction conditions) via a preliminary "activation" operation. This treatment may be performed either "in situ" (in the fluorination reactor) or in suitable apparatus designed to withstand the activation conditions.

After impregnation of the support, the catalyst is dried at a temperature of between 100° C. and 350° C., preferably 220° C. to 280° C., in the presence of air or nitrogen.

The dried catalyst is then activated in one or two steps with hydrofluoric acid, optionally in the presence of an oxidizing agent. The duration of this fluorination-mediated activation step may be between 6 and 100 hours and the temperature between 200 and 400° C.

A subject of the present invention is also a composition of the azeotropic or quasi-azeotropic type comprising 1-chloro-2,2-difluoroethane and trans-1,2-dichloroethylene.

Preferably, the azeotropic or quasi-azeotropic composition comprises 80 mol % to 95 mol % of 1-chloro-2,2-difluoroethane and from 5 mol % to 20 mol % of trans-1,2-dichloroethylene.

Advantageously, the azeotropic or quasi-azeotropic composition has a boiling point of between 32 and 119° C. at a pressure of between 1 and 10 bar abs.

The azeotropic composition may be obtained by extractive azeotropic distillation, liquid/liquid extraction or membrane separation.

EXAMPLES

Experimental Procedure:

HCC-140 and optionally 1,2-dichloroethylene and HF are fed separately into a monotubular Inconel reactor, heated by means of a fluidized alumina bath.

The pressure is regulated by means of a regulation valve located at the reactor outlet. The gases derived from the reaction are analyzed by gas chromatography.

The catalyst is first dried under a stream of nitrogen at 250° C. and the nitrogen is then gradually replaced with HF to terminate the activation with pure HF (0.5 mol/hour) at 350° C. for 8 hours.

Example 1

The catalyst used is a chromium oxide ($Cr_2O_3$). 35 g are activated as described above. HCC-140 and HF are then fed in at a mole ratio of 1:8 (10 g/hour of HF), at 230° C., 11 bar abs, with a contact time of 65 seconds.

The yield of F142 is 70% after 5 hours. After 30 hours, the yield is less than 30%.

Example 2

The catalyst used is a chromium oxide ($Cr_2O_3$) as in Example 1. 55 g are activated as described above. HCC-140, HF and chlorine are then fed in at an HCC-140/HF/chlorine mole ratio of 1:9:0.08 (17 g/hour of HF), at 230° C., 11 bar abs, with a contact time of 54 seconds.

The yield of F142 is 60% after 5 hours. After 100 hours, the yield is 62%.

Example 3

The catalyst used is a chromium oxide ($Cr_2O_3$) as in Example 1. 35 g are activated as described above. HCC-140, HF and chlorine are then fed in at an HCC-140/HF/chlorine mole ratio of 1:20:0.08 (30 g/hour of HF), at 225° C., 3 bar abs, with a contact time of 4 seconds.

The yield of F142 is 50% stable over a period of 500 hours.

Example 4

The catalyst used is a chromium oxide ($Cr_2O_3$) supported on alumina. 27 g are activated as described above. HCC-140 and HF are then fed in at an HCC-140/HF mole ratio of 1:8 (10 g/hour of HF), at 235° C., 11 bar abs, with a contact time of 45 seconds.

The yield of F142 is 70% after 5 hours. After 30 hours, the yield is less than 30%.

| Example | 1 | 2 | 3 | 4 |
|---|---|---|---|---|
| Catalyst | Bulk Cr oxide | Bulk Cr oxide | Bulk Cr oxide | Cr oxide on alumina |
| Amount (g) | 35 | 55 | 35 | 27 |
| HF/T112 mole ratio | 8 | 9 | 20 | 8 |
| HF (g/hour) | 10 | 17.5 | 30 | 10 |
| Chlorine/T112 mole ratio | 0 | 0.08 | 0.08 | 0 |
| T (° C.) | 230 | 230 | 225 | 235 |
| P (bar abs) | 11 | 11 | 3 | 11 |
| Contact time (seconds) | 65 | 54 | 4 | 45 |
| Yield (%) after 5 hours | 70 | 60 | 53 | 70 |
| Yield (%) after 30 hours | <30 | 61 | | <30 |
| Yield (%) after 100 hours | <10 | 62 | | |
| Yield (%) after 500 hours | | | 50 | |

Example 5

No catalyst is used. HCC-140 and HF are fed in at an HCC-140/HF mole ratio of 1:20 (30 g/hour of HF), at 225° C., 11 bar abs, with a contact time of 50 seconds.

The yield of F142 is 25% stable over a period of 500 hours.

The invention claimed is:

1. A process for manufacturing 1-chloro-2,2-difluoroethane from 1,1,2-trichloroethane and/or 1,2-dichloroethylene, comprising at least one step during which 1,1,2-trichloroethane and/or 1,2-dichloroethylene react(s) with hydrofluoric acid in the gas phase in the presence of an oxidizing agent, and in the presence or absence of a fluorination catalyst, to give a stream comprising 1-chloro-2,2-difluoroethane, hydrochloric acid, hydrofluoric acid and at least one compound C selected from the group consisting of 1-chloro-2-fluoroethylenes (cis and trans), 1,2-dichloro-2-fluoroethane and optionally unreacted 1,1,2-trichloroethane and 1,2-dichloroethylene.

2. A process for manufacturing 1-chloro-2,2-difluoroethane from 1,1,2-trichloroethane, comprising:
 (i) at least one step during which 1,1,2-trichloroethane reacts with hydrofluoric acid in the gas phase in the presence of an oxidizing agent, and in the presence or absence of a fluorination catalyst, to give a stream comprising 1-chloro-2,2-difluoroethane, hydrochloric acid, hydrofluoric acid and at least one compound C selected from the group consisting of 1,2-dichloroethylenes (cis and trans), 1-chloro-2-fluoroethylenes (cis and trans), 1,2-dichloro-2-fluoroethane and optionally unreacted 1,1,2-trichloroethane;
 (ii) at least one step of separating the compounds derived from the reaction step to give a stream A comprising hydrochloric acid and a stream B comprising hydrofluoric acid, 1-chloro-2,2-difluoroethane, at least one compound C and optionally 1,1,2-trifluoroethane;
 (iii) at least one step of separating the stream B to give an organic phase comprising 1-chloro-2,2-difluoroethane, at least one compound C and optionally unreacted 1,1,2-trichloroethane and a non-organic phase predominantly comprising HF;
 (iv) at least one step of separating the 1-chloro-2,2-difluoroethane from the organic phase obtained in (iii);
 (v) optionally, recycling into step (i) of the organic phase after the separation of step (iv); and
 (vi) optionally, recycling into step (i) of the non-organic phase derived from step (iii).

3. The process as claimed in claim 2, wherein, after the step of separating out the 1-chloro-2,2-difluoroethane, the organic phase comprises 1-chloro-2-fluoroethylene, 1,2-dichloroethylenes (cis and trans) and 1,2-dichloro-2-fluoroethane.

4. The process as claimed in claim 2, wherein the non-organic phase derived from step (iii) is purified such that the HF content is greater than or equal to 90% by weight before recycling into step (i).

5. The process as claimed in claim 4, wherein the purification comprises at least one distillation, performed at a temperature of between −23 and 46° C. and an absolute pressure of between 0.3 and 3 bar.

6. The process as claimed in claim 2, wherein the separation step (ii) comprises at least one distillation, performed at a temperature of between −60 and 120° C. and an absolute pressure of between 3 and 20 bar.

7. The process as claimed in claim 2, wherein the separation step (iii) comprises at least one decantation step, performed at a temperature of between −20 and 60° C.

8. The process as claimed in claim 2, wherein the separation step (iv) comprises at least one distillation, performed at a temperature of between 35 and 79° C. and an absolute pressure of between 0.3 and 4 bar.

9. The process as claimed in claim 1, wherein the temperature of the reaction step is between 150 and 400° C.

10. The process as claimed in claim 1, wherein the pressure at which the fluorination reaction is performed is between 1 and 20 bar absolute.

11. The process as claimed in claim 1, wherein the amount of hydrofluoric acid used in the reaction is between 5 and 40 mol per mole of HCC-140 and/or 1,2-dichloroethylene.

12. The process as claimed in claim 1, wherein the oxidizing agent is selected from the group consisting of oxygen and chlorine.

13. The process as claimed in claim 12, wherein the amount of oxidizing agent used is between 0.01 mol % and 20 mol % per mole of HCC-140 and/or 1,2-dichloroethylene.

14. A composition of the azeotropic or quasi-azeotropic type comprising from 80 mol % to 95 mol % of 1-chloro-2,2-difluoroethane and from 5 mol % to 20 mol % of trans-1,2-dichloroethylene.

15. A composition of the azeotropic or quasi-azeotropic type comprising 1-chloro-2,2-difluoroethane and trans-1,2-dichloroethylene, wherein the boiling point is between 32 and 119° C. at a pressure of between 1 and 10 bar abs.

16. The composition as claimed in claim 14, wherein the boiling point is between 32 and 119° C. at a pressure of between 1 and 10 bar abs.

* * * * *